(12) United States Patent
Wei

(10) Patent No.: US 9,271,698 B2
(45) Date of Patent: Mar. 1, 2016

(54) CART FOR ULTRASONIC IMAGING APPARATUS AND ULTRASONIC IMAGING SYSTEM

(75) Inventor: Bo Wei, Wuxi (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1457 days.

(21) Appl. No.: 12/957,145

(22) Filed: Nov. 30, 2010

(65) Prior Publication Data

US 2011/0128815 A1      Jun. 2, 2011

(30) Foreign Application Priority Data

Nov. 30, 2009   (CN) ........................ 2009 1 0225857

(51) Int. Cl.
H05K 7/14      (2006.01)
A61B 8/00      (2006.01)
B62B 5/00      (2006.01)

(52) U.S. Cl.
CPC ................. A61B 8/4405 (2013.01); B62B 5/00 (2013.01); Y10T 29/49826 (2015.01); Y10T 29/49959 (2015.01)

(58) Field of Classification Search
USPC ................. 600/437, 459, 104, 106, 102, 229; 710/303, 304; 307/149
See application file for complete search history.

(56) References Cited

U.S. PATENT DOCUMENTS

| | | | |
|---|---|---|---|
| 5,577,932 A | 11/1996 | Palmer | |
| 6,629,927 B1 | 10/2003 | Mesaros et al. | |
| 6,648,825 B1 | 11/2003 | Mesaros et al. | |
| 7,591,786 B2 * | 9/2009 | Holmberg | A61B 8/00 600/437 |
| 2003/0217600 A1 | 11/2003 | Collins et al. | |
| 2005/0247480 A1 | 11/2005 | Schulz | |
| 2006/0046561 A1 | 3/2006 | Lam et al. | |
| 2008/0161688 A1 | 7/2008 | Poland | |
| 2008/0221454 A1 | 9/2008 | Davidsen | |
| 2008/0225534 A1 | 9/2008 | Rus et al. | |
| 2009/0005686 A1 | 1/2009 | Yanagihara et al. | |
| 2009/0270727 A1 | 10/2009 | Zhao et al. | |
| 2010/0056913 A1 | 3/2010 | Hirakui et al. | |

FOREIGN PATENT DOCUMENTS

| | | |
|---|---|---|
| CN | 1471898 A | 2/2004 |
| CN | 1473548 A | 2/2004 |

(Continued)

OTHER PUBLICATIONS

Unofficial translation of SIPO Official Action and Search Report for CN Application No. 200910225857.2, dated Feb. 8, 2014.

*Primary Examiner* — Rexford Barnie
*Assistant Examiner* — Xuan Ly
(74) *Attorney, Agent, or Firm* — Armstrong Teasdale LLP

(57) ABSTRACT

A cart for use with an ultrasonic imaging apparatus, comprising: a supporting part, a cart body and a bottom part; said cart body is connected to the supporting part and the bottom part; said supporting part is provided with an interface thereon for supporting and connecting the ultrasonic imaging apparatus; said cart body is an elevator structure provided with a power cable therein for supplying power to the ultrasonic imaging apparatus; the lower portion of the supporting part and the upper portion of the bottom part are both provided with a power socket; said power cable is a coiled cord structure, and its two ends are connected to the two power sockets; a stretchable elastic component having elastic recovery is provided inside the coiled cord structure of the power cable.

17 Claims, 4 Drawing Sheets

(56) References Cited

FOREIGN PATENT DOCUMENTS

| | | |
|---|---|---|
| CN | 1655720 A | 8/2005 |
| CN | 1758878 A | 4/2006 |
| CN | 2906843 Y * | 5/2007 |
| CN | 101163986 A | 4/2008 |
| CN | 101238390 A | 8/2008 |
| CN | 101411626 A | 4/2009 |
| CN | 101541246 A | 9/2009 |
| CN | 101569537 A | 11/2009 |
| EP | 1271033 A2 | 1/2003 |

* cited by examiner

CART FOR ULTRASONIC IMAGING APPARATUS AND ULTRASONIC IMAGING SYSTEM

CROSS REFERENCE TO RELATED APPLICATIONS

This application claims the benefit of Chinese Patent Application No. 200910225857.2 filed Nov. 30, 2009, which is hereby incorporated by reference in its entirety.

BACKGROUND OF THE INVENTION

The present invention relates to the field of ultrasonic imaging apparatus, in particular to a cart in an ultrasonic imaging apparatus.

A cart-type ultrasonic system comprises a cart for supporting an ultrasonic imaging apparatus, the height of the cart is up-down adjustable. The cart is provided with a power cable therein in order to supply power to the ultrasonic imaging apparatus, as shown in FIG. 1, the power cable 10 connects an inlet and outlet of a DC current, the power cable 10 is a coiled cord which is retractile when the cart moves up and down. However, since the main material of the cable is resin, the ductility of the resin makes the power cable 10 could not return its original length but become longer after a period of use. When the cart lowers, the elongated power cable 10 may be in tangle, which can cause serious damage to the power cable 10 and cause safety problems.

BRIEF DESCRIPTION OF THE INVENTION

Embodiments described herein provide a cart used for an ultrasonic imaging apparatus to solve the above mentioned problem. The cart replaces the creep deformation of the power cable with an elastic deformation to realize better power cable management and to improve the reliability and safety of the power cable.

Moreover, embodiments described herein provide an ultrasonic imaging system that can resolve the above issue, which replaces the creep deformation of the power cable with an elastic deformation to realize better power cable management and to improve the reliability and safety of the power cable.

The cart used for an ultrasonic imaging apparatus provided in the present invention comprises: a supporting part, a cart body and a bottom part, said cart body is connected to the supporting part and the bottom part; said supporting part is provided with an interface thereon for supporting and connecting the ultrasonic imaging apparatus; said cart body is an elevator structure provided with a power cable therein for supplying power to the ultrasonic imaging apparatus; the lower portion of the supporting part and the upper portion of the bottom part are both provided with a power socket; said power cable is a coiled cord structure, and its two ends are connected to the two power sockets; a stretchable elastic component having elastic recovery is provided inside the coiled cord structure of the power cable.

In some embodiments, the stretchable elastic component is a spring.

In some embodiments, both ends of the spring are fastened at the two ends of the power cable respectively.

In some embodiments, both ends of the spring have a suspension ring, both ends of the power cable is fixed with a cable clip with a hole; a bolt or screw passes through the suspension ring of the spring and the hole on the cable clip fixed on the power cable to fasten the spring to the power cable.

In some embodiments, when the spring is in a natural state, its length is equal to a length of the coiled cord structure of the power cable in its natural state.

In some embodiments, the cart body comprises a fixed end in the lower section of the cart body and a moving end which is movable up and down in the upper section of the cart body; said fixed end is connected and fixed to the bottom part, said moving end is connected to the supporting part; one end of the power cable fastened with a spring is fixed to the fixed end of the cart body, and the other end thereof is fixed to the moving end of the cart body.

In some embodiments, the bottom part comprises a plurality of supporting legs having wheels.

The ultrasonic imaging system provided by the present invention comprises an ultrasonic imaging apparatus and a cart for supporting the ultrasonic imaging apparatus; said cart comprises: a supporting part, a cart body and a bottom part, said cart body is connected to the supporting part and the bottom part; said supporting part is provided with an interface thereon for supporting and connecting the ultrasonic imaging apparatus; said cart body is an elevator structure provided with a power cable therein for supplying power to the ultrasonic imaging apparatus; the lower portion of the supporting part and the upper portion of the bottom part are both provided with a power socket; said power cable is a coiled cord structure, and its two ends are connected to the two power sockets; a stretchable elastic component having elastic recovery is provided inside the coiled cord structure of the power cable.

In some embodiments, the stretchable elastic component is a spring, the both ends thereof are fastened at the two ends of the power cable respectively.

In some embodiments, both ends of the spring have a suspension ring, both ends of the power cable is fixed with a cable clip with a hole; a bolt or screw passes through the suspension ring and the hole on the cable clip fixed on the power cable to fasten the spring to the power cable.

In some embodiments, when the spring is in a natural state, its length is equal to a length of the coiled cord structure of the power cable in its natural state.

In some embodiments, the cart body comprises a fixed end in the lower section of the cart body and a moving end which is movable up and down in the upper section of the cart body; said fixed end is fixed to the bottom part, said moving end is connected to the supporting part; one end of the power cable fastened with a spring is fixed to the fixed end of the cart body, and the other end thereof is fixed to the moving end of the cart body.

In some embodiments, the bottom part comprises a plurality of supporting legs having wheels.

In this invention, a stretchable elastic component having elastic recovery is provided inside the coiled cord structure of the power cable, which can reduce or eliminate creep deformation of the coiled cord structure of the power cable to ensure the power cable can be restored and returns to its original normal length after a long period of use. In addition, the spring in the present invention also works as a guider for the movement of the power cable by making the power cable move straightly, whereby the power cable's scratching and crashing with other components can be prevented when moving randomly. The present invention enhances the safety of the cart and prolongs the service life of the power cable. The present invention also has the advantages of having a simple structure and low cost.

DETAILED DESCRIPTION OF THE INVENTION

Hereinafter, embodiments of the invention will be explained in details with reference to the attached drawings. The present invention is not limited to the embodiments.

Figure 1:
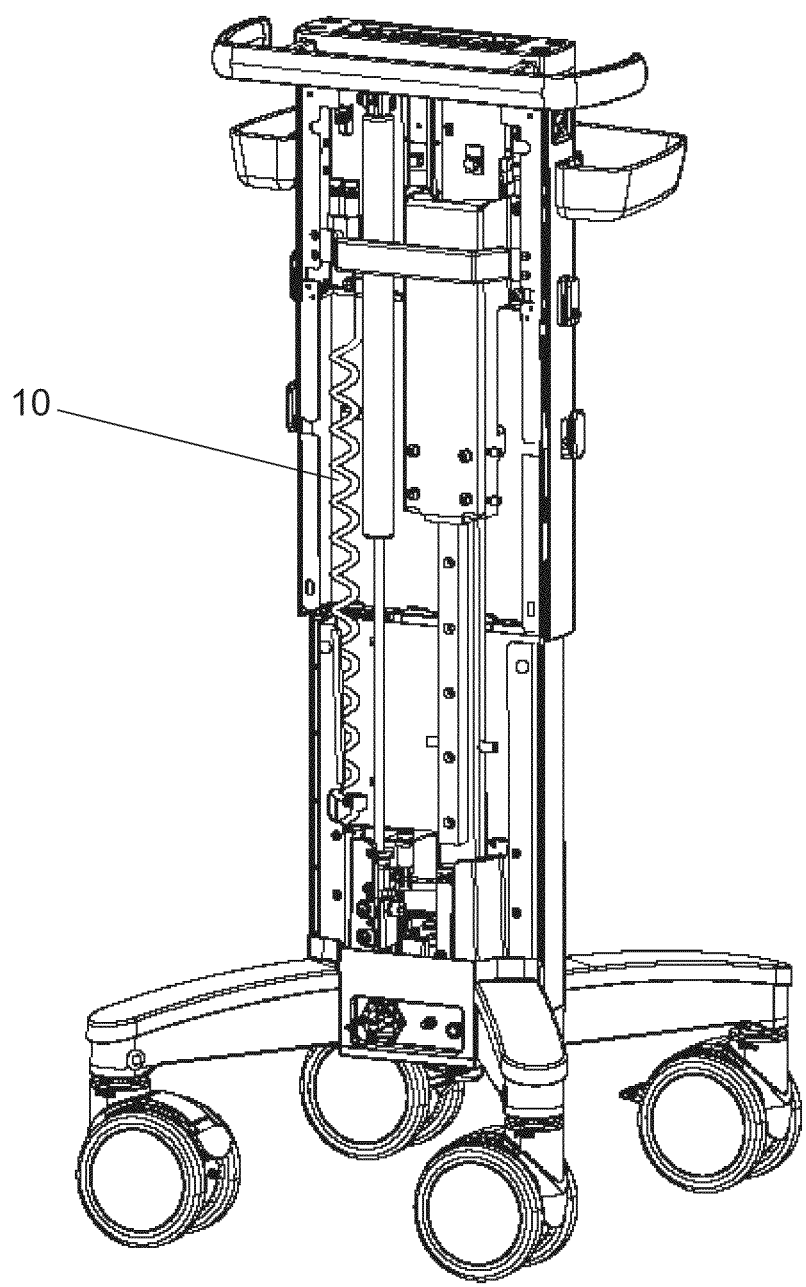
FIG. 1 is a structural schematic diagram of a cart in the prior art.
Figure 2:
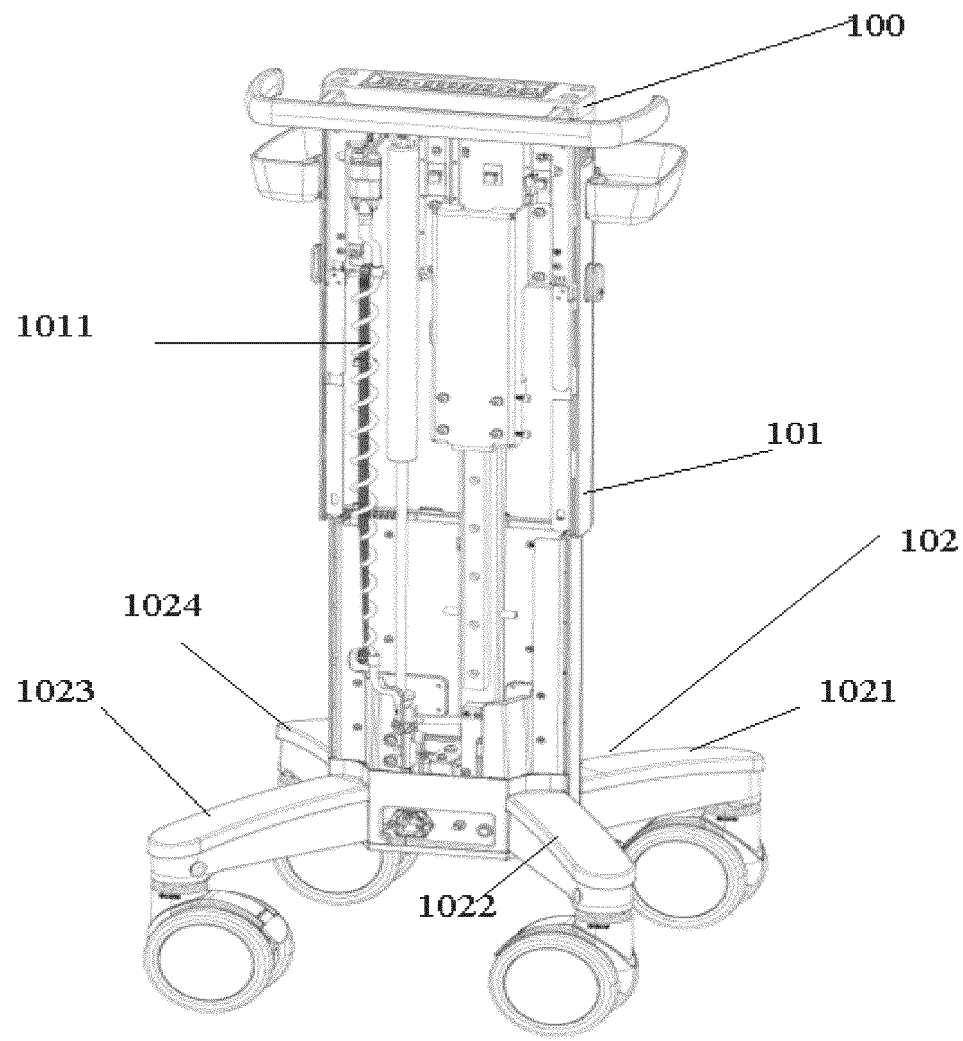
FIG. 2 is a structural schematic diagram of a cart of the present invention.

As shown in FIG. 2, a cart used for an ultrasonic imaging apparatus provided by the present invention comprises: a supporting part 100, a cart body 101 and a bottom part 102, said cart body 101 is connected to the supporting part 100 and the bottom part 102; said supporting part 100 is provided with an interface thereon for supporting and connecting the ultrasonic imaging apparatus (not shown in the figure); said cart body 101 is an elevator structure provided with a power cable 1011 therein for supplying power to the ultrasonic imaging apparatus; the lower portion of the supporting part 100 and the upper portion of the bottom part 102 are both provided with a power socket (not shown in the figure); said power cable 1011 is a coiled cord structure, and its two ends are connected to the two power sockets.

Figure 3:
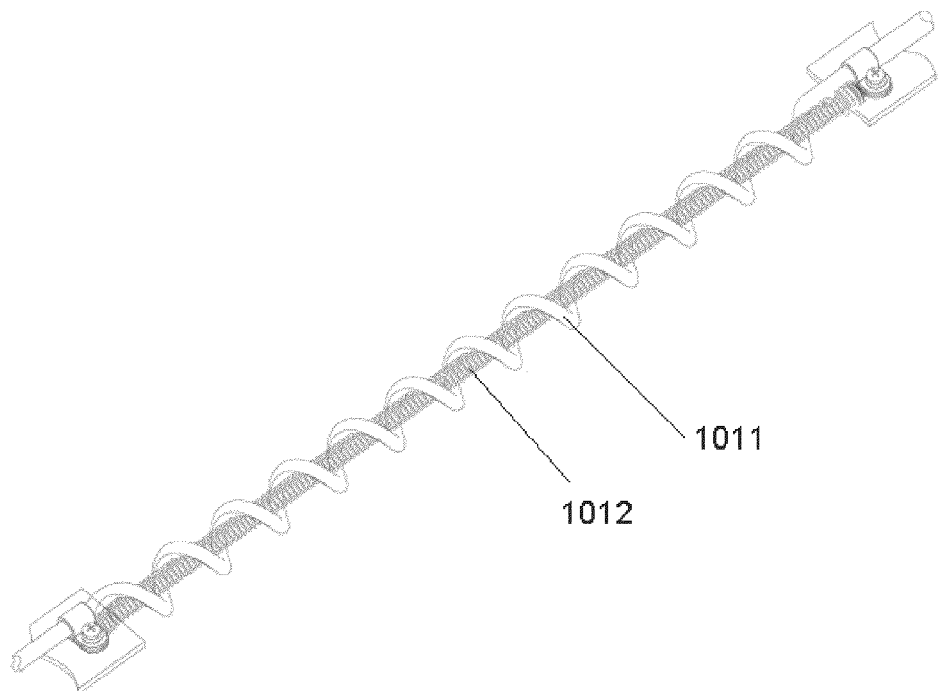
FIG. 3 is a structural schematic diagram of the power cable and spring mated together in the present invention.
Figure 4:
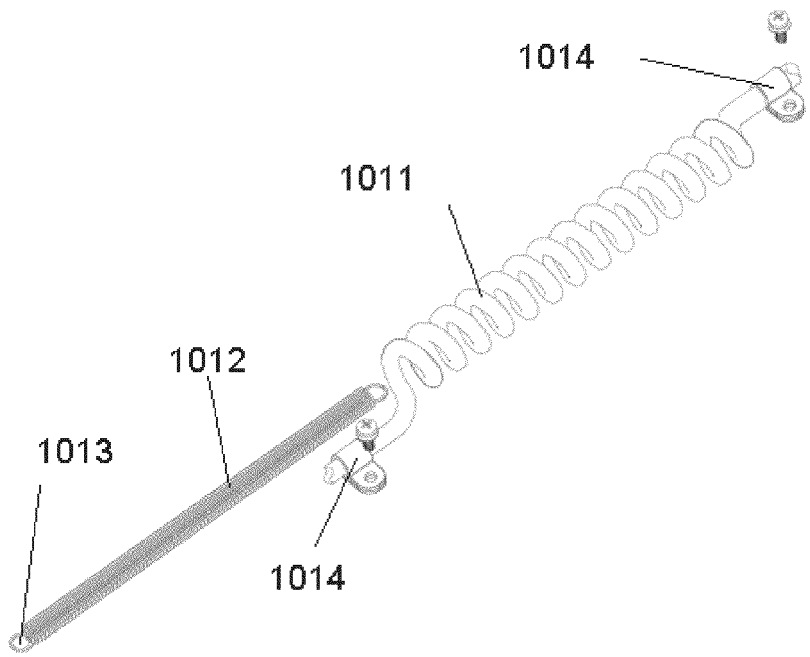
FIG. 4 shows exploded structural schematic diagram of the power cable and spring mated together.
Figure 5:
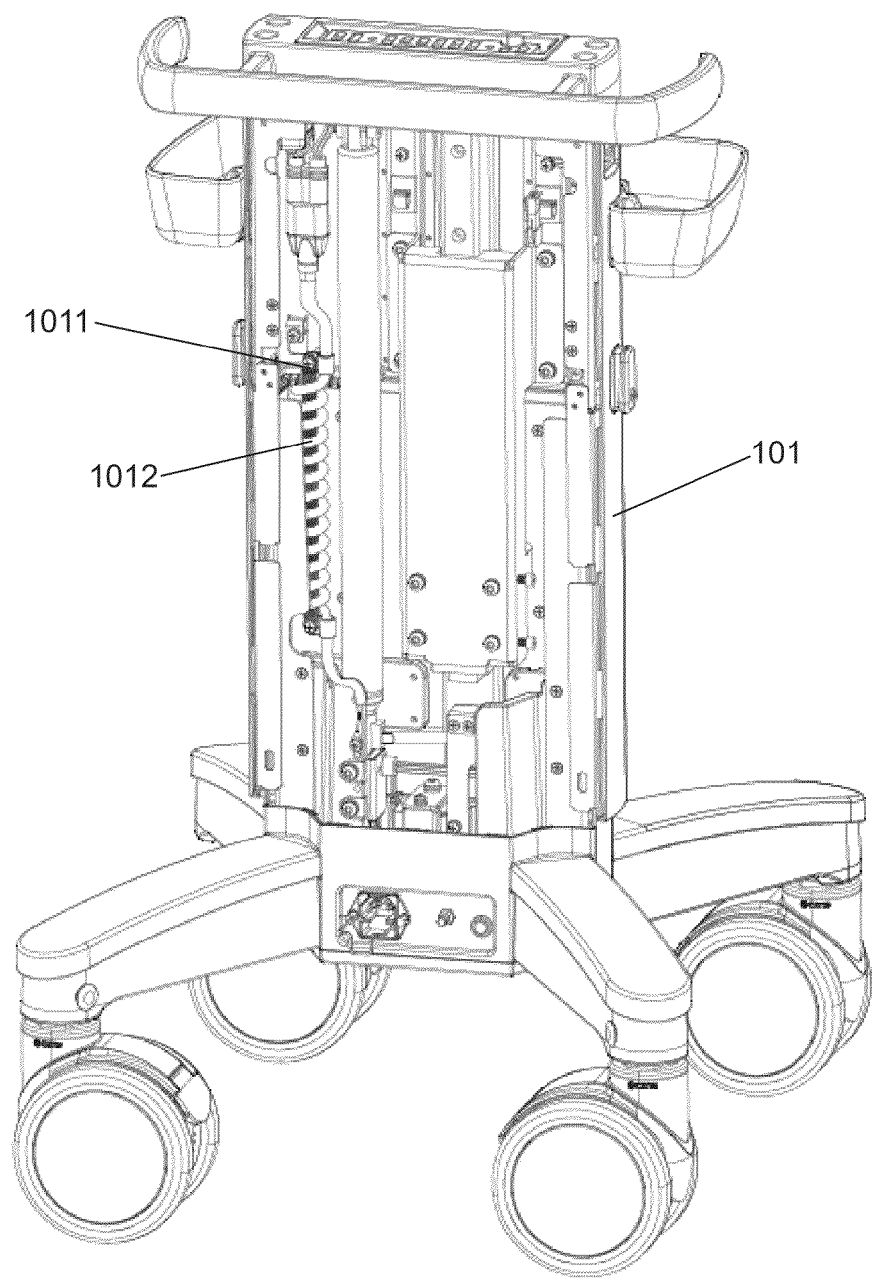
FIG. 5 is a structural schematic diagram of the cart in another state in the present invention.

Now referring to FIG. 3 in the meanwhile, a spring 1012 is designed and assembled inside the power cable 1011, when the spring 1012 is in a natural state, its length is equivalent to a length of the coiled cord structural part of the power cable 1011 in its natural state. Of course, they may be not equal as well. The two ends of the spring 1012 are fastened to the two ends of the power cable 1011. As shown in the embodiment of FIG. 4, fastening of the spring 1012 and the power cable 1011 is implemented through the following structure: the two ends of the spring 1012 are provided with a suspension ring 1013, a pair of cable clips 1014 with a hole thereon are fastened to the two ends of the power cable 1011, the spring 1012 and the power cable 1011 are fastened together by passing a screw or a bolt through the suspension ring 1013 of the spring 1012 and the hole on the cable clips 1014 fastened onto the power cable 1011. In order to optimize the effect of the spring 1012 on the power cable 1011, one end of the power cable 1011 having the spring 1012 is fixed to the fixed end of the cart body 101, and the other end is fixed to the moving end of the cart body 101. When the moving end of the cart body 1011 moves up and down, the spring 1012, together with the power cable 1011, compresses or expands up and down. As shown in FIG. 2, when the cart body 101 is lifted, the power cable 1011 and the spring 1012 therein is in a stretching state; FIG. 5 shows that when the cart body 101 is lowered, the power cable 1011 and the spring 1012 therein is in a compression state. Since the spring 1012 has the characteristic of elastic deformation, the defect of creep deformation of the power cable 1011 is alleviated, and the power cable 1011 can still be restored and returns to its original normal length after a long period of use.

The spring 1012 in the present invention also has a function of guiding the power cable 1011 in movement and making the power cable 1011 move straightly so that the power cable's scratching and crashing with other components can be prevented during random movement.

Said spring 1012 is a tension spring. Of course, other stretchable components having elastic recovery can also be used to replace the spring 1012.

Said bottom part 102 comprises a plurality of supporting legs 1021, 1022, 1023, 1024 with wheels. In the embodiment, there are four supporting legs to enable the cart to move conveniently.

What is claimed is:

1. A cart for use with an ultrasonic imaging apparatus, said cart comprising:
    a supporting part comprising:
        an interface configured to support and couple to the ultrasonic imaging apparatus; and
        a lower portion comprising a first power socket;
    a bottom part comprising an upper portion comprising a second power socket; and
    a cart body coupled to said supporting part and said bottom part, said cart body comprising an elevator structure comprising an internal power cable configured to supply power to the ultrasonic imaging apparatus, said power cable comprising:
        a coiled cord structure comprising a first end coupled to said first power socket and a second end coupled to said second power socket; and
        a spring having elastic recovery, wherein a first point of said coiled cord structure is anchored to a first point of said spring using a first fastening mechanism and a second point of said coiled cord structure is anchored to a second point of said spring using a second fastening mechanism such that said first point and said second point of said coiled cord structure cannot extend beyond said respective first and second points of said spring, and wherein said first and second fastening mechanisms further anchor said coiled cord structure and said spring to said cart body.

2. A cart according to claim 1, wherein said first and second points of said spring each comprises a respective first and second suspension ring, said first and second points of said coiled cord structure are coupled to said cart body with respective first and second cable clips each having a hole extending therethrough, each of said first and second suspension rings and cable clip holes sized to receive said first and second fastening mechanisms therein to fasten said spring to said coiled cord structure.

3. A cart according to claim 2, wherein, when said spring is in a first state, a length thereof is equal to a length of said coiled cord structural part in a respective first state.

4. A cart according to claim 2, wherein said cart body further comprises a lower section and an upper section configured to move vertically, said lower section is coupled to said bottom part, said upper section is coupled to said supporting said second end of said power cable coupled to said lower section, said first end of said power cable coupled to said upper section.

5. A cart used for an ultrasonic imaging apparatus according to claim 1, wherein said bottom part further comprises a plurality of supporting legs with wheels.

6. An ultrasonic imaging system, comprising:
    an ultrasonic imaging apparatus; and
    a cart configured to support said ultrasonic imaging apparatus, said cart comprising:
        a supporting part comprising an interface configured to support and couple to the ultrasonic imaging apparatus and a lower portion comprising a first power socket;
        a bottom part comprising an upper portion comprising a second power socket; and
        a cart body coupled to said supporting part and said bottom part, said cart body comprising an elevator structure comprising an internal power cable configured to supply power to the ultrasonic imaging apparatus, said power cable comprising a coiled cord structure comprising a first end coupled to said first power socket and a second end coupled to said second power socket, and a spring having elastic recovery, wherein a first point of said coiled cord structure is anchored to a first point of said spring using a first fastening mechanism and a second point of said coiled cord structure is anchored to a second point of said spring using a second fastening mechanism such that said first point and said second point of said coiled cord structure cannot extend beyond said respective first and second points of said spring, and wherein said first and second fastening mechanisms further anchor said coiled cord structure and said spring to said cart body.

7. An ultrasonic imaging system according to claim 6, wherein said first and second points of said spring each comprises a respective first and second suspension ring, said first and second points of coiled cord structure are coupled to said cart body with respective first and second cable clips each having a hole extending therethrough, each of said first and second suspension rings and cable clip holes sized to receive said first and second fastening mechanisms therein to fasten said spring to said coiled cord structure.

8. An ultrasonic imaging system according to claim 7, wherein, when said spring is in a first state, a length thereof is equal to a length of said coiled cord structural part in a respective first state.

9. An ultrasonic imaging system according to claim 8, wherein said cart body further comprises a lower section and an upper section configured to move vertically, said lower section is coupled to said bottom part, said upper section is coupled to said supporting said second end of said power cable coupled to said lower section, said first end of said power cable coupled to said upper section.

10. An ultrasonic imaging system according to claim 6, wherein said bottom part further comprises a plurality of supporting legs with wheels.

11. A method of assembling an ultrasonic imaging system having an ultrasonic imaging apparatus and a cart, the cart including a supporting part, a bottom part, and a cart body, said method comprising:
coupling the supporting part to the ultrasonic imaging apparatus, the supporting part including a lower portion having a first power socket;
providing a second power socket within the bottom part; and
coupling the cart body to the supporting part and the bottom part, the cart body having an elevator structure including an internal power cable configured to supply power to the ultrasonic imaging apparatus, the power cable including a coiled cord structure with a first end coupled to the first power socket and a second end coupled to the second power socket, the power cable further including a spring having elastic recovery, wherein a first point of the coiled cord structure is anchored to a first point of the spring using a first fastening mechanism and a second point of the coiled cord structure is anchored to a second point of the spring using a second fastening mechanism such that the first point and the second point of the coiled cord structure cannot extend beyond the respective first point and second points of the spring, and wherein the first and second fastening mechanisms further anchor the coiled cord structure and the spring to the cart body.

12. A method according to claim 11, said method further comprising coupling the spring to the power cable.

13. A method according to claim 12, wherein coupling the spring to the power cable further comprises:
coupling a first suspension ring at the first point of the spring to the first point of the coiled cord structure; and
coupling a second suspension ring at the second point of the spring to the second point of the coiled cord structure
coupling the first point of the coiled cord structure to the cart body with a first cable clip; and coupling the second point of the coiled cord structure to the cart body with a second cable clip.

14. A method according to claim 13, wherein coupling the spring to the power cable further comprises:
inserting the first fastening mechanism through a first hole within the first cable clip and through the first suspension ring; and
inserting the second fastening mechanism through a second hole within the second cable clip and through the second suspension ring.

15. A method according to claim 11, wherein coupling the cart body to the supporting part and the bottom part comprises:
coupling a lower section of the cart body to the bottom part and to the second end of the power cable; and
coupling an upper section to the supporting part and to the first end of the power cable, the upper section configured to move vertically.

16. A method according to claim 11, further comprising coupling a plurality of supporting legs with wheels to the bottom part.

17. A cart according to claim 1, wherein said spring is stretchable between a first position and a second position, wherein in the first position said spring has a first length, and wherein in the second position, said spring has a second length that is at least twice the first length.

* * * * *